(12) United States Patent
Maier

(10) Patent No.: US 6,329,660 B1
(45) Date of Patent: Dec. 11, 2001

(54) METHOD OF DERIVING SUNLIGHT INDUCED FLUORESCENCE FROM RADIANCE MEASUREMENTS AND DEVICES FOR EXECUTING THE METHOD

(75) Inventor: Stefan Walter Maier, Gilching (DE)

(73) Assignee: Dutsches Zentrum fur Luft-und Ramfahrt E.V., Bonn (DE)

( * ) Notice: Subject to any disclaimer, the term of this patent is extended or adjusted under 35 U.S.C. 154(b) by 0 days.

(21) Appl. No.: 09/294,357

(22) Filed: Apr. 20, 1999

(30) Foreign Application Priority Data

Apr. 22, 1998 (DE) ............................................... 198 17 843

(51) Int. Cl.⁷ .................................................. G01N 21/64
(52) U.S. Cl. ..................................... 250/459.1; 250/458.1
(58) Field of Search .............................. 250/459.1, 458.1, 250/461.1, 208.1, 559.4, 361, 362; 356/417, 318

(56) References Cited

U.S. PATENT DOCUMENTS

| 3,598,994 | 8/1971 | Markle . |
| 4,671,662 | 6/1987 | Zupanick et al. . |
| 4,708,475 | 11/1987 | Watson . |
| 5,062,713 | 11/1991 | Farquharson et al. . |
| 5,298,741 | 3/1994 | Walt et al. . |
| 5,567,947 | 10/1996 | Kebabian . |

OTHER PUBLICATIONS

McFarlane et al., "Plant stress detection by remote measurement of fluorescence", *Applied Optics*, vol. 19 No. 19, pp. 3287–3289, (1980).

*Primary Examiner*—Georgia Epps
*Assistant Examiner*—Richard Hanig
(74) *Attorney, Agent, or Firm*—Browdy and Niemark

(57) ABSTRACT

To derive sunlight induced fluorescence from radiance measurements, a first radiance measurement is taken inside an atmospheric absorption band, and an additional radiance measurement is taken outside of the atmospheric absorption band. Images of sunlight-induced fluorescence are obtained with the aid of a camera. Air- or spaceborne spectrometers and image points on non-fluorescent objects are used to determine the radiance conditions on the ground and the influence of the atmosphere.

14 Claims, 7 Drawing Sheets

METHOD OF DERIVING SUNLIGHT INDUCED FLUORESCENCE FROM RADIANCE MEASUREMENTS AND DEVICES FOR EXECUTING THE METHOD

FIELD OF THE INVENTION

The invention relates to a method of deriving sunlight induced fluorescence from radiance measurements, and devices for executing the method.

REVIEW OF THE RELATED TECHNOLOGY

In remote sensing, reflection measurements are often used to determine the status of vegetation. In the process, the light reflected by the vegetation is detected in more or less narrow channels (e.g. frequency bands). For verification, and to preclude for atmospheric influence, measurements are also taken with spectrometers a few meters above the ground.

Within the scope of a measurement campaign, these types of measurements are taken for wheat cultures (e.g. fields), for example. FIG. 6 shows a typical reflectance spectrum. A notable feature is a peak at 762 nm in the so-called infrared plateau, indicated by a circle. This peak never occurs in laboratory measurements using artificial lighting.

To ascertain the cause of this peak, the following procedure must be considered in the determination of a reflectance spectrum: First, the light reflected by a white reference standard (i.e., a surface having a known reflection factor of nearly 100%) is measured. Then, the light radiated back from the test object is detected. FIG. 7 shows these two measurements, from which the reflectance spectrum in FIG. 6 was calculated by computing the quotient and subsequent multiplication with the reflectance spectrum of the white reference standard.

FIG. 7 clearly shows the $o_2A$ absorption band of the atmosphere at 762 nm. Because the measurements contain a larger relative error due to the lower signals, measuring errors were determined to be the cause of the peak. The peak, however, was intended to be statistically distributed once with an upward orientation and once with a downward orientation.

In the course of further measurements, however, the peak was always upwardly-oriented. A systematic error must therefore have been present. Because the error only occurred in green vegetation, however, the cause could only be chlorophyll fluorescence.

In biology, chlorophyll fluorescence is used to characterize the state of the photosynthesis apparatus of plants. Up to now, active measurement methods have generally been used to measure the fluorescent light emitted by some materials, particularly green plant parts, under daylight conditions. In these methods, the material to be tested is irradiated with a pulsed or modulated light source in addition to solar illumination. The fluorescent light additionally generated by this light is detected with the aid of the lock-in measuring technique. For short distances and point measurements, LEDs are used as the light sources (refer to the periodical "Rev. Sci. Instrum." 1975, Vol. 46, No. 5, pp. 538 through 542).

LASERS are used for larger distances and imaging detection (refer to the journal "Remote Sensing of Environment" 1994, No. 47, pp. 10 through 17). In these active methods, however, only the additionally-generated fluorescent light, and not be fluorescent light caused by solar irradiation, is measured. Hence, information can only be obtained regarding the fluorescence quantum yield.

SUMMARY OF THE INVENTION

It is the object of the invention to further develop a method of deriving sunlight induced fluorescence from radiance measurements, without using an additional light source, and to provide devices for carrying out method of detecting sunlight induced fluorescence, particularly chlorophyll fluorescence of green plants, from a distance of several meters, and for providing on imaging detection of fluorescence, especially chlorophyll fluorescence of green plants.

Thus, a method of deriving the fluorescence from a reflection signals was development. This method is described below.

The present invention provides a method and devices for carrying out a method of detecting sunlight induced fluorescence, especially chlorophyll fluorescence of green plants, from a distance of several meters, and for imaging detection of fluorescence.

The method of the invention is based on the "filling" of broadband atmospheric absorption bands in the reflection signals with fluorescent light. The starting point is that the radiance $L_\gamma$ at the detector is formed as follows:

$$L_{so} = (R \cdot L_\lambda^0 + L^{fluorescence}) \cdot T_\lambda + L_\lambda^{path} \qquad (1)$$

Here R represents the unknown reflectance factor of the material to be tested, which is assumed to be wavelength-independent in the tested spectral range. The radiance of the sunlight at the object is represented by $L_\lambda^0$; $L^{fluorescence}$ represents the fluorescence radiance, which is also assumed to be wavelength-independent; $T_\lambda$ represents the transmission factor of the atmosphere between the object and the sensor; and $L_\lambda^{path}$ represents the radiance of the so-called "path light", i.e. the light scattered directly to the sensor from the atmosphere between the object and the sensor.

The radiances for a least two wavelengths located closely together, namely a radiance inside an atmospheric absorption band and a further radiance lying outside of the atmospheric absorption band, are measured, so the wavelength independence of the reflection factor R and the fluorescence radiance $L^{fluorescence}$ is assured.

To detect the chlorophyll fluorescence at 762 nm, a distance between the two measured wavelengths of, for example, up to 10 nm is possible. Knowledge of the exact position of the wavelengths is not critical. The only condition that must be met for solving the resulting system of equations is different radiances of the illumination for the different wavelengths. This condition is met in the range of the atmospheric absorption bands of water vapor and molecular oxygen between 660 nm and 1000 nm.

In most cases, the prerequisite of a wavelength-independent reflection factor R and a wavelength-independent fluorescence radiance $L^{fluorescence}$ can be circumvented by an advantageous modification of the method of the invention, in which a measurement is taken on both sides of the absorption band instead of one measurement being taken outside of the absorption band. In this way, for the same wavelength, two measurements having very different incident radiances are obtained, and the fluorescence radiance can therefore be determined.

In comparison to the fluorescence-measurement methods used up to now, the advantages of the invention are that an additional light source can be omitted, and it is therefore possible to detect the sunlight induced fluorescence of larger surfaces. In addition, fewer requirements are placed on the detection system with respect to spectral resolution.

Hence, a spectral resolution of, for example, 10 nm is sufficient in the range of the $O_2A$ absorption band around 762 nm. This is turn permits the use of less-sensitive detectors, or measurements over larger distances. Moreover, it is possible to take a fluorescence measurement in the spectral range of 650 nm to 800 nm, which is important for a detection of the chlorophyll fluorescence.

In accordance with an advantageous embodiment of the invention, image points of non-fluorescent objects are used to determine the radiance conditions on the ground, and the influence of the atmosphere, for deriving sunlight induced fluorescence light from image data obtained with an air- or spaceborne imaging spectrometer.

BRIEF DESCRIPTION OF THE DRAWING

The above and other objects and the nature and advantages of the present invention will become more apparent from the following detailed description of embodiments taken in conjunction with drawings, wherein.

DETAILED DESCRIPTION OF THE PREFERRED EMBODIMENT

Depending on the aerosol content, the influence of the atmosphere between the measured object and the sensor from measured distances of up to a few hundred meters can be disregarded. This means that the transmission factor $T_\lambda = 1$ and the path light $L_\lambda^{path}$ are both equal to zero. The resulting evaluation equation is as follows:

$$L^{fluorescence} = \frac{L_1 - \frac{L_1^0}{L_2^0}L_2}{1 - \frac{L_1^0}{L_2^0}} \quad (2)$$

As the evaluation equation (2) shows, a relative calibration suffices for two detectors that detect the fluorescence radiances $L_1^0$ and $L_2^0$. If the absolute value of the fluorescence radiance is to be determined, the two detectors that detect the fluorescence radiances $L_1$ and $L_2$ must be calibrated absolutely. Otherwise, a relative calibration of the detectors with respect to one another suffices.

In remote sensing, the influence of the atmosphere between the object and sensor cannot be disregarded. Furthermore, in most cases it is not possible to take a direct measurement of the sunlight incident at the object. The method described below must be used. The following evaluation equation results from Eq. (1):

$$k_3 \cdot L^{fluorescence} = L_1 - k_1 \cdot L_2 - k_2 \quad (3)$$

$$k_1 \equiv \frac{L_1^0 \cdot T_1}{L_2^0 \cdot T_2}$$

$$k_2 \equiv L_1^{path} - k_1 \cdot L_2^{path}$$

$$k_3 \equiv T_1 - k_1 \cdot T_2$$

Figure 1:
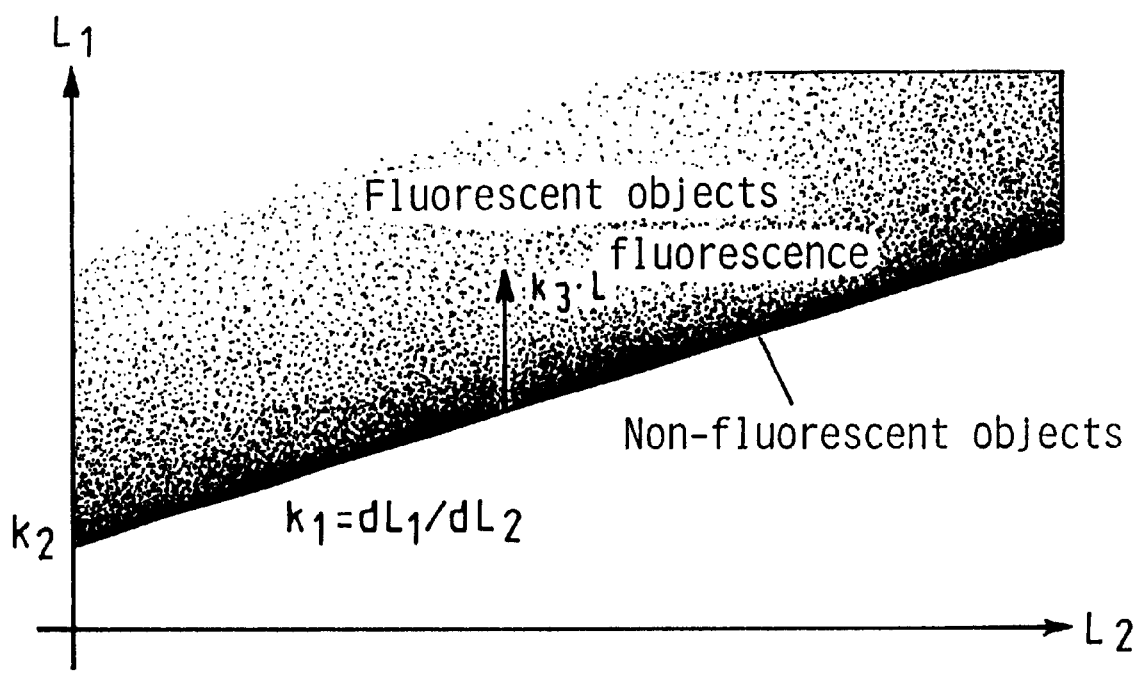
FIG. 1 is a graphical view of the invention in the form of a straight line on which radiances of non-fluorescent objects are shown, while fluorescent objects are shown in the half-plane above the straight line.

In FIG. 1, a radiance $L_1$ is shown on the ordinate, and an radiance $L_2$ is shown on the abscissa. The radiances of non-fluorescent objects lie on a straight line. The fluorescent objects lie in the upper half-plane. The distance in the ordinate, or $L_1$, direction is equal to $k_3 \cdot L^{fluorescence}$. If the radiance $L_1$ is shown above the radiance $L_2$ of non fluorescent objects, $k_1$ corresponds to the slope and $k_2$ corresponds to the offset section of the fitted straight lines. The fluorescence radiance of fluorescent objects can then be calculated form the above equation.

The value $k_3$ cannot be derived only from the measurements of the radiances $L_1$ and $L_2$, however. The Fluorescence radiance can therefore be derived only in relative units. For an absolute value, however, ground measurements must be taken, or the transmission factor of the atmosphere $T_1$ and $T_2$ must be known from other measurements or simulation.

Figure 2:
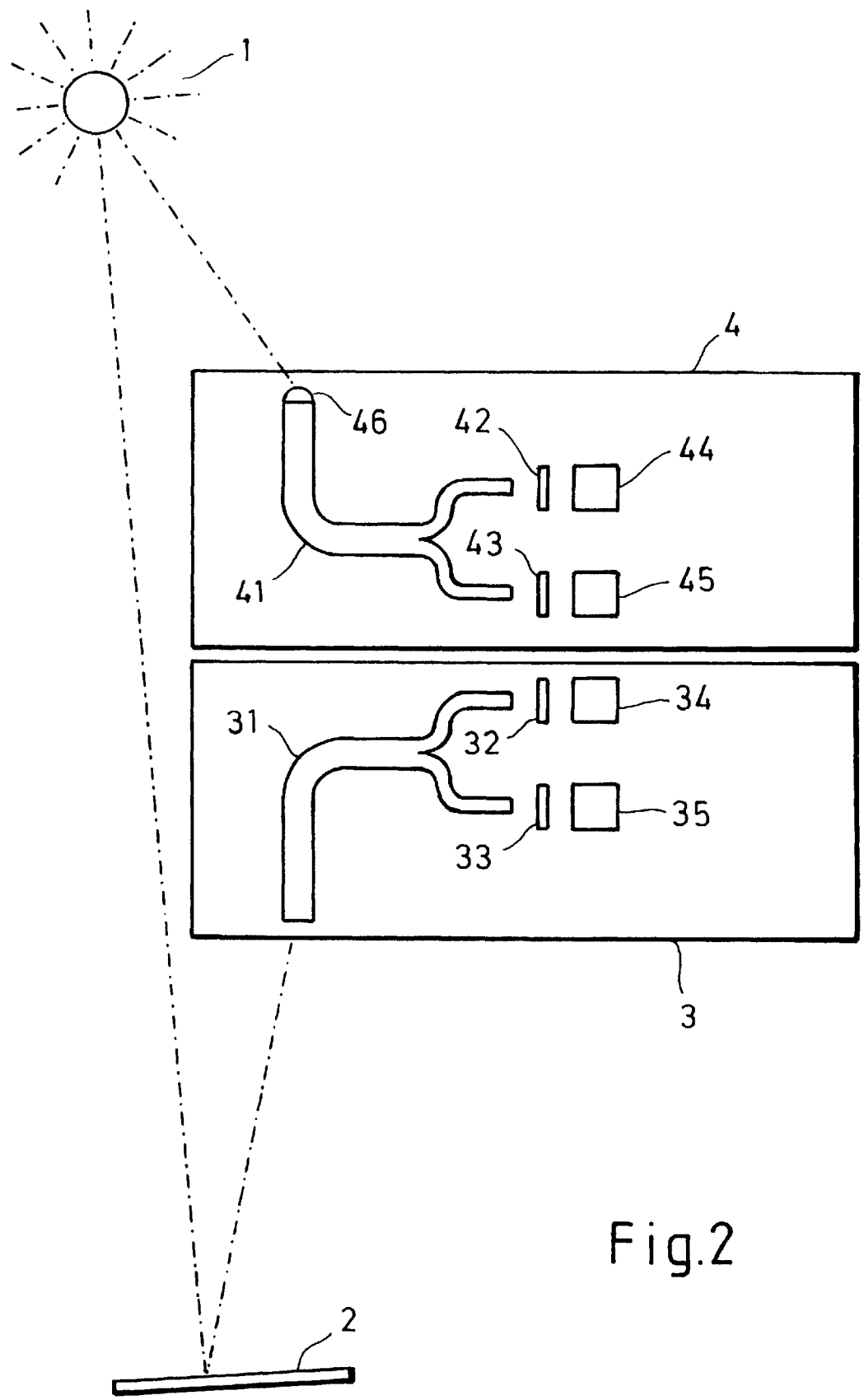
FIG. 2 is a schematic view of a first embodiment of a device for detecting fluorescence from a distance of only a few meters in the range of the $O_2A$ absorption band.

FIG. 2 show an embodiment of a device for executing the method of the invention with respect to a detection of fluorescence over a distance of several meters in the range of the $O_2A$ absorption band around 762 nm. With the aid of a optical waveguide 31, a lower detection unit 3 in FIG. 2 records light emitted by a measured object 2 illuminated by the sun 1. This optical waveguide 31 comprises a plurality of individual multimode fibers that are statistically distributed onto two detectors 34 and 35. As a result, any image information is blurred and the two detectors 34 and 35 "see" the same regions of the measured object.

A detection unit 4 for detecting irradiated light, show near the top of FIG. 2, has basically the same design as the detection unit 3, namely a optical waveguide 41 and two detectors 44 and 45. In Addition, however, a diffusor 46 is disposed in front of the optical waveguide 41 for increasing its acceptance angle.

Interference band-pass filters 32 and 42 having a central wavelength of 752 nm and a bandwidth of 5 nm are disposed in front of the detectors 34 and 44 for the spectral selection. Interference band-pass filters 33 and 43 are likewise disposed in front of the detectors 35 and 45, the filters having a central wavelength of 762 nm with a bandwidth of 5 nm. A precision of ±2 nm is sufficient for the position of the central wavelength and the bandwidth of the interference filters. Only the accordance of the spectral transmission characteristics of the filters 32 and 42, sharing one pass-band and of the filters 33 and 43 sharing the other pass-band respectively is important.

To verify the functioning capability of this device, it was simulated with the aid of a spectrometer. The spectral selection of the channels was achieved by a grating. (In principle, any arbitrary spectrometer having a sufficient spectral resolution could be used.) The measurement was taken from a distance of about one meter. This corresponded to a measured-point diameter of 20 cm.

To verify that the fluorescence is actually detected, the fluorescence kinetics of the photosynthesis apparatus of a green plant (Kautsky effect) is recorded. At the same time, a currently-conventional, active measurement method, PAM fluorometry, was used to take the measurements. The measuring distance was about 1 cm, with a surface of 0,2 cm² being detected.

Figure 3:
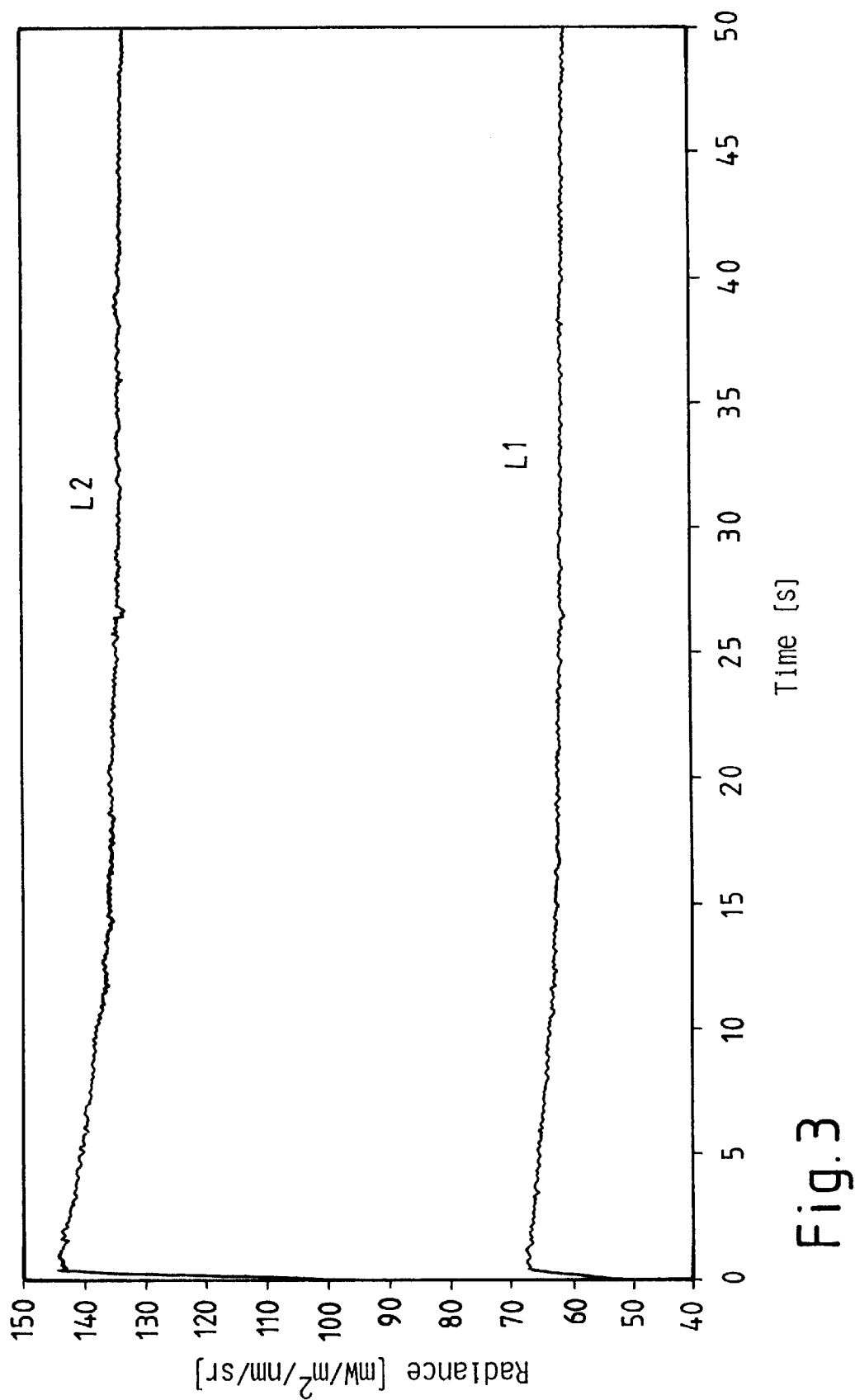
FIG. 3 is a graphical view of the course over time of reflected radiances measured with the aid of a spectrometer in or before the $O_2A$ absorption band.
Figure 4:
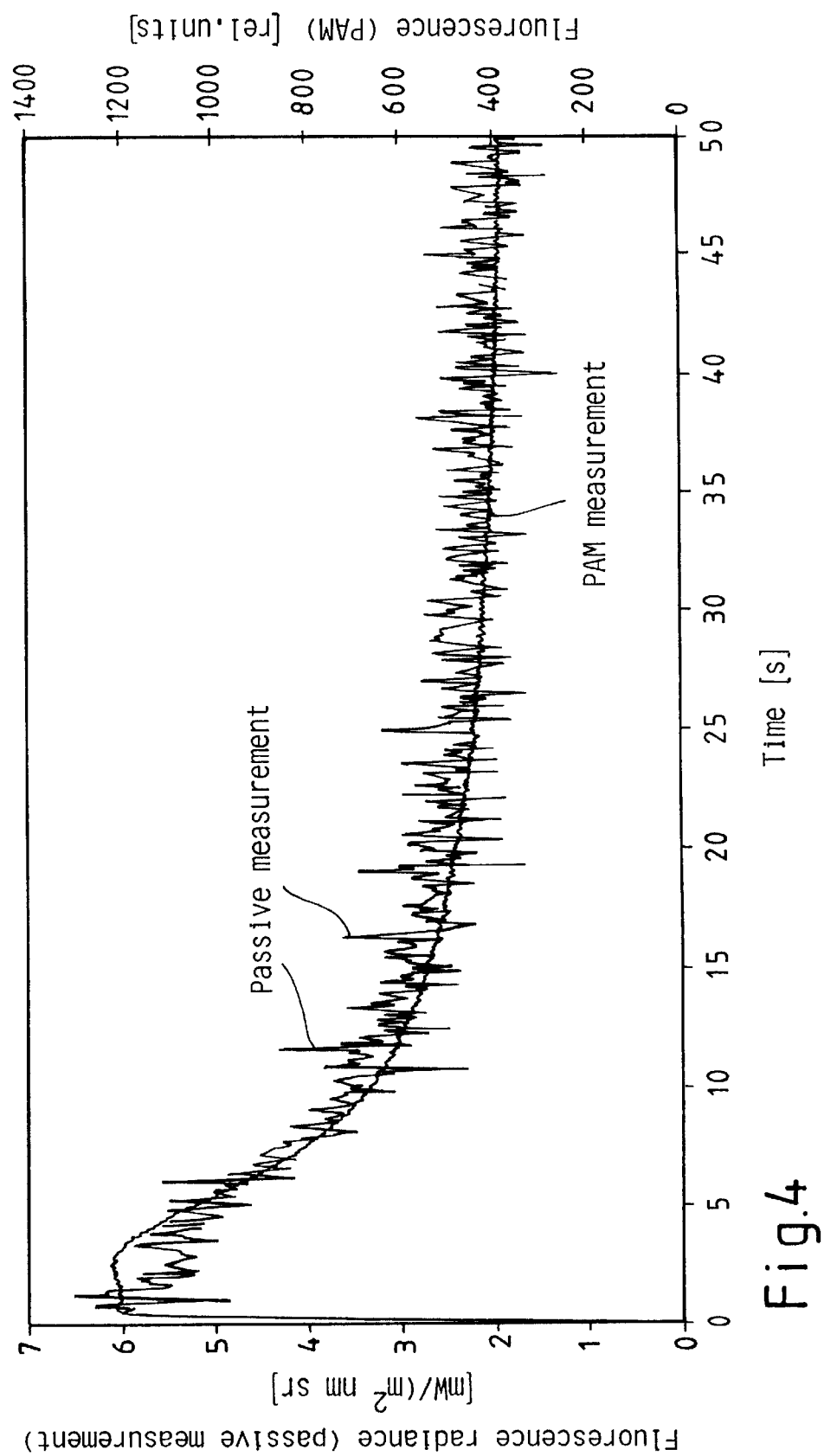
FIG. 4 is a graphical view of the course over time of a fluorescence derived from FIG. 3 according to Eq. (2) and measured with a PAM fluorometer, with the time being shown in seconds (s) on the abscissa and the fluorescence radiance being shown in mW/(m²nm sr) on the ordinate.

FIG. 3 shows the course over time of the reflected radiances of vegetation, which were measured with the aid of the spectrometer, in ($L_1$) or before ($L_2$), of the $O_2A$ absorption band. FIG. 4 shows the course over time of the fluorescence derived from this according to Eq. (2) and measured with a PAM fluorometer. The two measurements matched very well, despite the differently-sized measuring surface.

Figure 5:
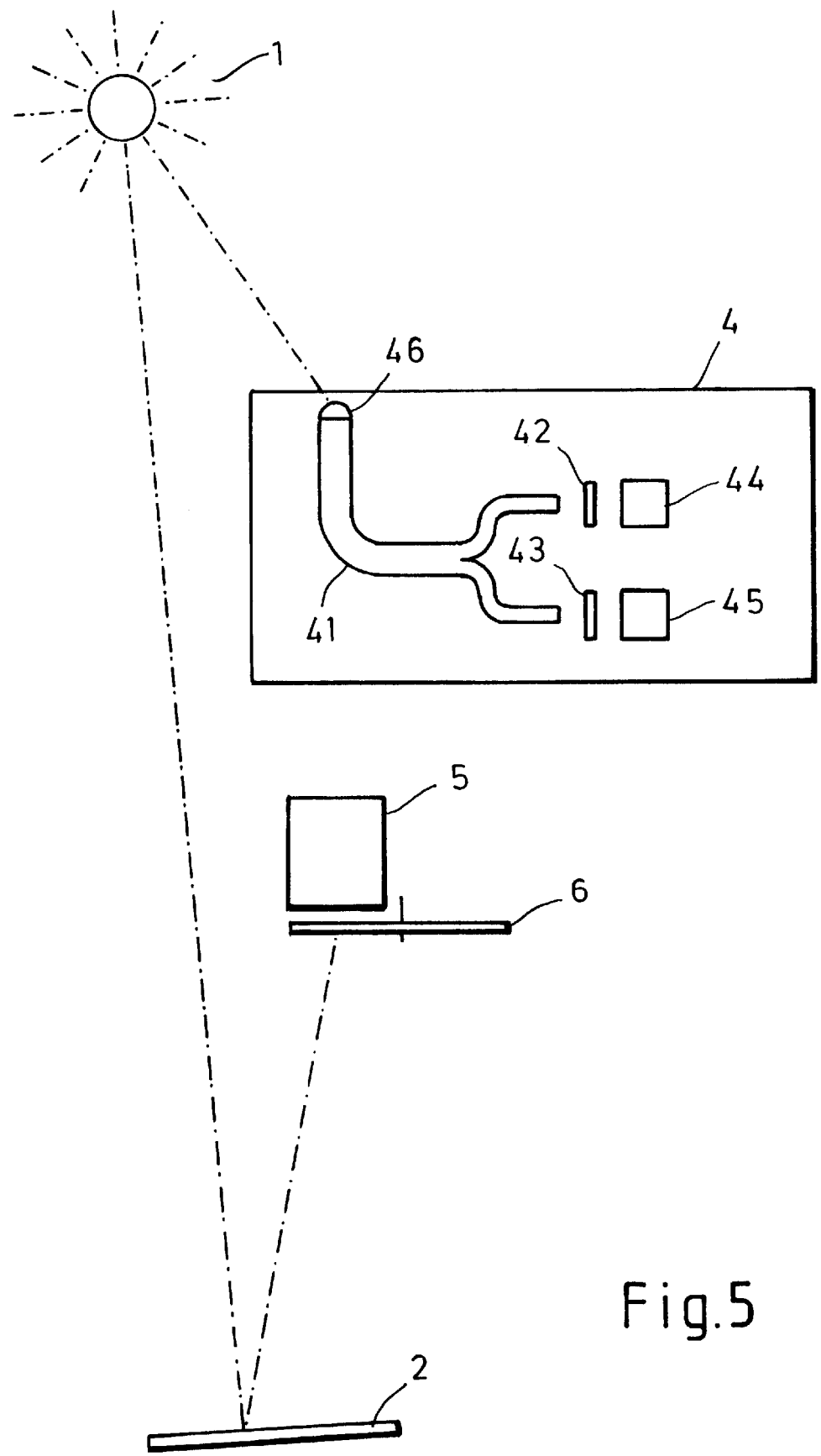
FIG. 5 is a schematic view of a preferred embodiment of a device for carrying out the method of imaging detection of fluorescence.
Figure 6:
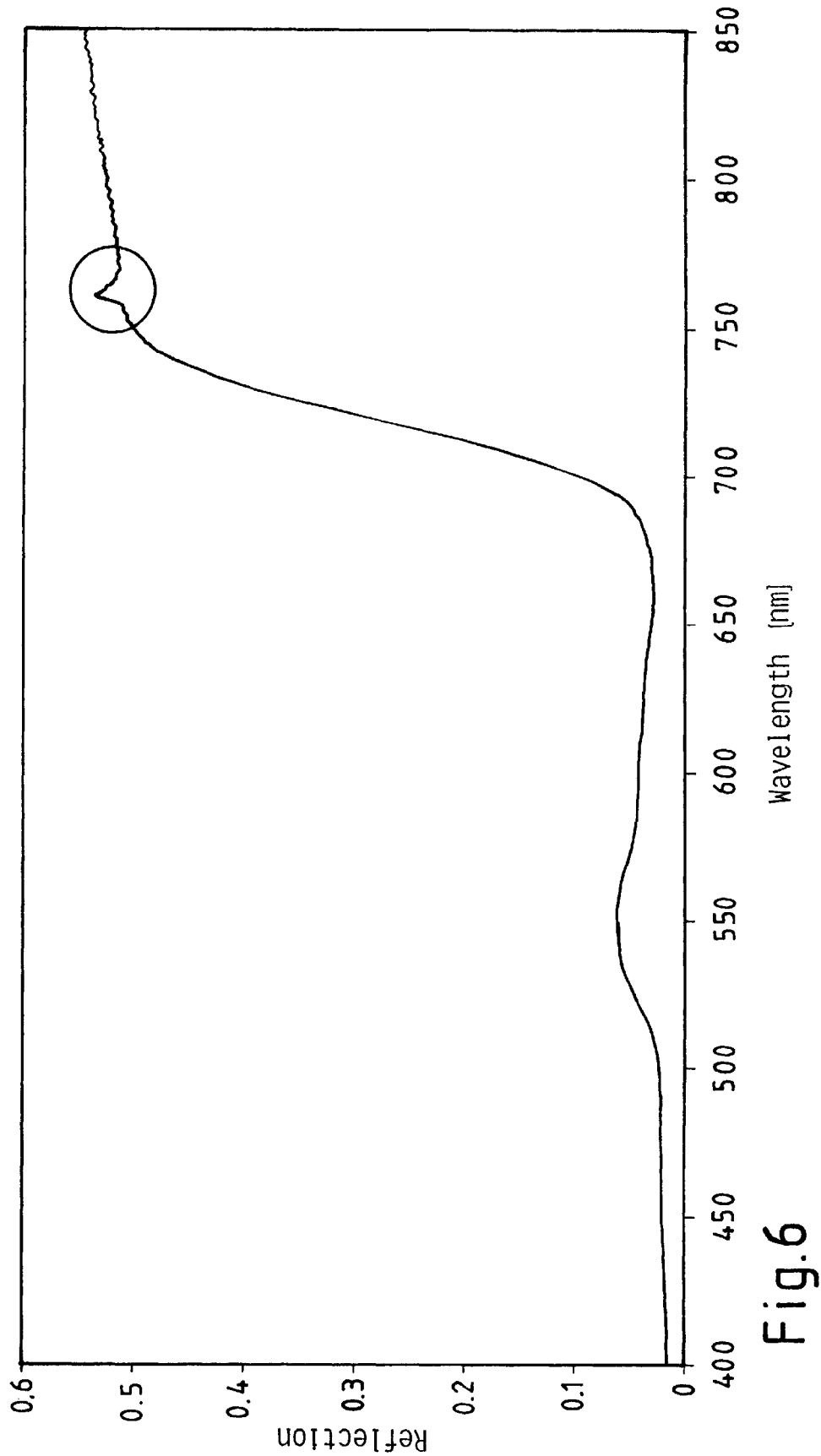
FIG. 6 graph of a typical reflectance spectrum, with the wavelength being shown in nm on the abscissa and the reflection being shown on the ordinate.
Figure 7:
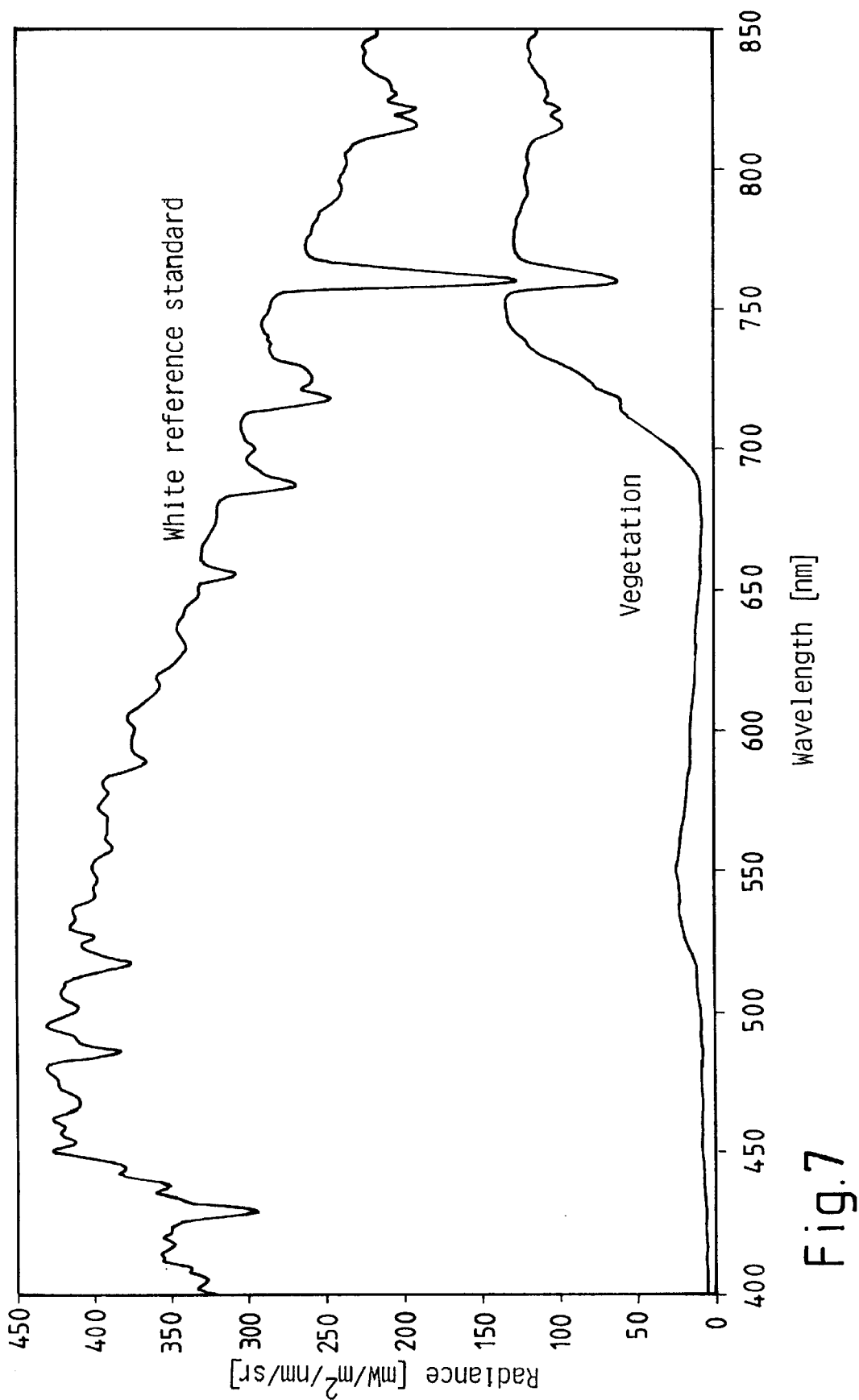
FIG. 7 is a graphical view showing a radiance measurements from which the reflectance spectrum in FIG. 6 is calculated by computing the quotient and subsequent multiplication.

FIG. 5 schematically shows an embodiment of a device for imaging detection of fluorescence. The lower detection unit is replaced by a CCD camera 5. To avoid the cost of a second CCD-camera, only one CCD-camera equipped with a filter wheel 6 is provided. The interference band-pass filters, not shown in detail, are accommodated on the filter wheel 6, permitting switching between the two detection channels.

According to the invention, a method is created for deriving sunlight induced fluorescence from reflection measurements. Thus, it is possible to derive the fluorescence from passive measurements with simple spectrometers. This in turn permits the use of air- or spaceborne spectrometers for large-surface detection of the chlorophyll fluorescence and therefore the photosynthetic state of the vegetation.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means and materials for carrying out various disclosed functions may take a variety of alternative forms without departing from the invention.

Thus the expressions "means to . . . " and "means for . . . " as may be found in the specification above and/or in the claims below, followed by a functional statement, are intended to define and cover whatever structural, physical, chemical or electrical element or structure may now or in the future exist which carries out the recited function, whether or not precisely equivalent to the embodiment or embodiments disclosed in the specification above; and it is intended that such expressions be given their broadest interpretation.

LIST OF REFERENCE CHARACTERS

1 Sun
2 Measured object
3 Detection unit
31 Optical waveguide
32, 33 Interference band-pass filters
34, 35 Detectors
4 Detection unit
41 Optical waveguide
42, 43 Interference band-pass filters
44, 45 Detectors
46 Diffusor
5 CCD camera
6 Filter wheel

What is claimed is:

1. A method of deriving sunlight induced fluorescence from radiance measurements, comprising:
   taking a first radiance measurement inside an atmospheric absorption band;
   taking a second radiance measurement outside of the atmospheric absorption band;
   deriving the sunlight induced fluorescence from image data obtained with the aid of air- or spaceborne spectrometers, and
   using image points of non-fluorescent objects to determine radiance conditions on the ground and an influence of the atmosphere.

2. A device for deriving sunlight induced fluorescence from radiance measurements by a method that includes: taking a first radiance measurement inside an atmospheric absorption band; and taking a second radiance measurement outside of the atmospheric absorption band, and for detecting sunlight induced fluorescence from a measured object (2) at a distance of several meters from the device, the device comprising:
   (a) a first detection unit (3) recording light emitted by the measured object (2) when the measured object is illuminated by the sun, the first detection unit comprising:
      a first optical waveguide (31) having a first light receiving end and comprising a first plurality of individual multimode fibers, the first plurality of fibers being divided fork-like, adjacent a light-emitting end, into two first sections of approximately equal size, and
      respective first detectors (34, 35) disposed adjacent the two first sections, the first detectors including respective first interference band-pass filters (32, 33) disposed between the two first sections of the first optical waveguide (31) and the first detectors (34, 35); and
   (b) a second detection unit (4) receiving irradiated sunlight, the second detection unit comprising:
      a second optical waveguide (41) having a second light-receiving end and comprising a second plurality of individual multimode fibers, the second plurality of fibers being divided fork-like, adjacent a light-emitting end, into two second sections of approximately equal size,
      respective second detectors (44, 45) disposed adjacent the two second sections, including respective second interference band-pass filters (42, 43) disposed between the two second sections of the second optical waveguide (41) and the second detectors (44, 45), and
      a diffusor (46) disposed adjacent the light-receiving end of the second optical waveguide (41) and orientable toward the sun.

3. The device according to claim 2, wherein
   the band-pass filters include two different passbands, and wherein
   in each of the first interference band-pass filters (32, 33) and the second interference band-pass filters (42, 43), one filter includes one of the two passbands and another filter includes another one of the two passbands.

4. The device according to claim 3, wherein the passbands are less than approximately 10 nm apart.

5. The device according to claim 3, wherein one of the passbands is centered on 762 nm.

6. A device for deriving sunlight induced fluorescence from radiance measurements by a method that includes: taking a first radiance measurement inside an atmospheric absorption band; and taking a second radiance measurement outside of the atmospheric absorption band, and for imaging detection of sunlight induced fluorescence from a measured object (2) at a distance of several meters from the device, the device comprising:

(a) a detection unit (4) comprising:

an optical waveguide (41) comprising a plurality of individual multimode fibers, the plurality of fibers being divided fork-like, adjacent a light-emitting end thereof, into two sections of approximately equal size, respective detectors (44, 45) disposed adjacent the two sections, including respective interference band-pass filters (42, 43) provided between the two sections of the optical waveguide (41) and the detectors (44, 45), and a diffusor (46) disposed adjacent the light-receiving end of the optical waveguide (41) and orientable toward the sun;

(b) a CCD-camera (5) for recording light emitted by a measured object (2) illuminated by the sun (1); and (c) a filter wheel (6) disposed between the CCD camera and the measured object.

7. The device according to claim 6, wherein the sunlight induced fluorescence includes chlorophyll fluorescence of green plants.

8. The device according to claim 6, wherein the filter wheel includes filters with different passbands.

9. The device according to claim 8, wherein the passbands are less than approximately 10 nm apart.

10. The device according to claim 8, wherein one of the passbands is centered on 762 nm.

11. A device for deriving sunlight induced fluorescence from radiance measurements by a method that includes: taking a first radiance measurement inside an atmospheric absorption band; and taking a second radiance measurement outside of the atmospheric absorption band, and for detecting sunlight induced fluorescence from a measured object (2), the device comprising:

(a) a pair of detection units (3, 4), each of the detection units comprising:

an optical waveguide (31, 41) comprising a plurality of individual multimode fibers extending between a bundled end intended to receive light and a divided end intended to emit light, the plurality of fibers being fork-like divided into two sections at the divided end;

a respective detector (34,35; 44,45) disposed adjacent each of the two sections of the divided end;

a first interference band-pass filter (32,42) disposed between a first one of the sections and the respective detector adjacent thereto; and a second interference band-pass filter (33,43) disposed between a second one of the sections and the respective detector adjacent thereto;

(b) wherein in each of the two detection units the first interference band-pass filter thereof includes a first passband centered on a first wavelength, and wherein in each of the two detection units the second interference band-pass filter thereof includes a second passband centered on a second wavelength different from the first wavelength;

whereby, a first one of the detection units receives at the bundled end thereof light emitted by the measured object (2) when the measured object is illuminated by the sun (1), a second one of the detection units receives at the bundled end thereof radiated sunlight, and the sunlight induced fluorescence is detectable by a comparison of signals from the detectors.

12. The device according to claim 11, wherein the plurality of multimode fibers are arranged such that light from the bundled end is statistically distributed onto the two detectors.

13. The device according to claim 11, including means for calculating the sunlight induced fluorescence from signals from the detectors.

14. The device according to claim 13, wherein the calculating means includes imaging means for imaging detection of sunlight induced fluorescence.

* * * * *